United States Patent
Nakahara et al.

(10) Patent No.: US 11,382,338 B2
(45) Date of Patent: Jul. 12, 2022

(54) ORGANIC ACID GLYCOSIDE CONTAINED IN COFFEE BEANS

(71) Applicant: SUNTORY HOLDINGS LIMITED, Osaka (JP)

(72) Inventors: Koichi Nakahara, Osaka (JP); Keiko Iwasa, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 522 days.

(21) Appl. No.: 15/026,321

(22) PCT Filed: Oct. 3, 2014

(86) PCT No.: PCT/JP2014/076522
§ 371 (c)(1),
(2) Date: Mar. 31, 2016

(87) PCT Pub. No.: WO2015/050240
PCT Pub. Date: Apr. 9, 2015

(65) Prior Publication Data
US 2016/0242431 A1    Aug. 25, 2016

(30) Foreign Application Priority Data
Oct. 3, 2013    (JP) .............................. JP2013-208667

(51) Int. Cl.
| | |
|---|---|
| A23F 5/46 | (2006.01) |
| C07H 13/04 | (2006.01) |
| A23F 5/14 | (2006.01) |
| A23F 5/10 | (2006.01) |
| A23F 5/24 | (2006.01) |
| A23L 27/10 | (2016.01) |
| A23F 5/36 | (2006.01) |

(52) U.S. Cl.
CPC .................. *A23F 5/46* (2013.01); *A23F 5/10* (2013.01); *A23F 5/14* (2013.01); *A23F 5/24* (2013.01); *A23F 5/36* (2013.01); *A23L 27/10* (2016.08); *A23L 27/11* (2016.08); *C07H 13/04* (2013.01)

(58) Field of Classification Search
CPC ...... A23F 5/10; A23F 5/24; A23F 5/36; A23F 5/46; A23L 27/11; C07H 13/04
See application file for complete search history.

(56) References Cited

U.S. PATENT DOCUMENTS

| | | | | |
|---|---|---|---|---|
| 2002/0155210 A1* | 10/2002 | Hardesty | ................. | A23F 5/243 426/594 |
| 2005/0181044 A1* | 8/2005 | Romero | ................. | A23F 5/385 424/464 |
| 2005/0181107 A1* | 8/2005 | Naef | ......................... | A23F 5/02 426/594 |
| 2006/0115517 A1* | 6/2006 | Tsuchiya | ............... | A61K 31/198 424/439 |
| 2006/0115518 A1* | 6/2006 | Tsuchiya | ............... | A61K 31/198 424/439 |
| 2006/0251607 A1* | 11/2006 | Golz-Berner | ............ | A61K 8/97 424/74 |
| 2008/0113077 A1* | 5/2008 | Leloup | ....................... | A23F 5/02 426/595 |
| 2008/0311271 A1* | 12/2008 | Sugimoto | ................. | A23F 5/04 426/595 |
| 2009/0011095 A1* | 1/2009 | Yamane | .................. | A23F 5/243 426/115 |

(Continued)

FOREIGN PATENT DOCUMENTS

| | | |
|---|---|---|
| JP | 2001-524484 A | 12/2001 |
| JP | 2003-212782 A | 7/2003 |

(Continued)

OTHER PUBLICATIONS

Onishi, N. "From Dung to Brew, No Aftertaste: Civets' Droppings Yield Coveted Coffee Beans." The New York Times Apr. 10, 2010: p. 6.*
Table 21.2 "Chemical composition of green coffee beans (% dry weight basis)." 1999. Food Chemistry. Eds. Belitz et al. Springer-Verlag: Berlin, p. 876.*
Akihisa, Toshihiro, et al., "Melanogenesis-Inhibitory Saccharide Fatty Acid Esters and Other Constituents of the Fruits of *Morinda citrifolia* (Noni)," Chemistry & Biodiversity, 2012, vol. 9(6), pp. 1172-1187.
Aspinall, Gerald O., et al., "Base-catalyzed Degradations of Carbohydrates. VII. Alkaline Degradation of 3,6-Di-O-Substituted Hexoses," Canadian Journal of Chemistry, 1975, vol. 53(14), pp. 2171-2177.

(Continued)

*Primary Examiner* — Nikki H. Dees
(74) *Attorney, Agent, or Firm* — Faegre Drinker Biddle & Reath LLP (57) ABSTRACT

The present invention provides a novel organic acid glycoside existing in coffee beans and a use thereof.

Formula 1

[Formula 1]

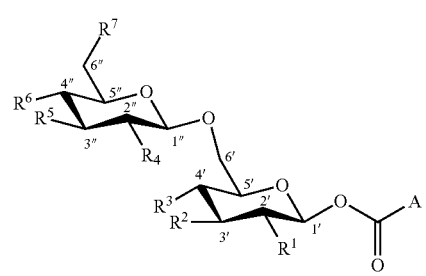

wherein, each of $R^1$ to $R^7$ is independently selected from a group consisting of H, OH, $NH_2$, $OCH_3$, $OC(O)CH_3$, and $NHCOCH_3$;
A is selected from $C_1$ to $C_6$ alkyl or $C_1$ to $C_6$ alkenyl, and the $C_1$ to $C_6$ alkyl or $C_1$ to $C_6$ alkenyl may be substituted by methyl or ethyl.

5 Claims, 7 Drawing Sheets

(56) References Cited

U.S. PATENT DOCUMENTS

| | | | |
|---|---|---|---|
| 2011/0052754 A1* | 3/2011 | Foley | A23L 33/105 426/2 |
| 2012/0040027 A1* | 2/2012 | Milo | A23F 5/02 424/725 |

FOREIGN PATENT DOCUMENTS

| | | |
|---|---|---|
| JP | 2004-081053 A | 3/2004 |
| JP | 2009-219488 A | 10/2009 |
| WO | WO-99/26956 A1 | 6/1999 |
| WO | WO-2010124936 A1 | 11/2010 |

OTHER PUBLICATIONS

Bosso, Claude, et al., "Use of carbon-13 in mass spectrometry. Study of the fragmentation of disaccharides," Organic Mass Spectrometry, 1978, vol. 13(8), pp. 477-482.

Bradbury, A.G.W., et al., "Carboxyatractyligenin and Atractyligenin Glycosides in Coffee," 18th Sci. Int. Cafe, 1999, pp. 71-77.

De, K. K., et al., "The Acid Hydrolysis of Glycosides, III. Hydrolysis of O-Methylated Glucosides and Disaccharides," Carbohydrate Research, 1967, vol. 4(1), pp. 72-77.

Excoffier, Gérard, et al., "Synthesis of oligosaccharides on a polymeric support. VII. Stereospecificity of glycosylation reactions: synthesis of isomaltose," Carbohydrate Research, 1976, vol. 46(2), pp. 215-226.

Maier, Hans Gerhard, et al., "Bestimmung von Diterpen-Glykosiden im Bohnenkaffee," Z. Lebensm. Unters. Forsch., 167, 1978, pp. 105-107.

Morikawa, Toshio, et al., "Medicinal Flowers. XXX. Eight New Glycosides, Everlastosides F-M, from the Flowers of Helichrysum arenarium," Chemical Pharmaceutical Bulletin, 2009, vol. 57(8), pp. 853-859.

Roy, Nirmolendu, et al., "The Synthesis of Three Fully Acetylated Aldobiouronic Acid Methyl Esters, Including 6-O-(Methyl 2,3,4-tri-O-acetyl-α-D-glucopyranosyluronate)-tetra-0-acetyl-β-D-glucopyranose," Journal of Organic Chemistry, 1968, vol. 33(4), pp. 1559-1562.

Weckerle, B., et al., "Linalool diaccharides as flavour precursors from green coffee beans (*Coffea arabica*)," Eur Food Res Technol, 2003, 216: 6-10.

Weckerle, Bernhard, et al., "3-Methylbutanoyl and 3-methylbut-2-enoyl disaccharides from green coffee beans (*Coffea arabica*)," Phytochemistry 60, 2002, pp. 409-414.

Yu, Yang, et al., "Monoterpenoids from the Fruit of Gardenia jasminoides," Helvetica Chemica Acta, 2010, vol. 93 (4), pp. 763-771.

International Search Report dated Oct. 28, 2014 for PCT/JP2014/076522.

EP Application 14850777.5—Extended European Search Report dated Jun. 9, 2017.

\* cited by examiner

ORGANIC ACID GLYCOSIDE CONTAINED IN COFFEE BEANS

This application is the National Stage of International Application No. PCT/JP2014/076522, filed Oct. 3, 2014, and claims benefit of Japanese Application No. 2013-208667 filed on Oct. 3, 2013.

TECHNICAL FIELD

The present invention relates to a novel organic acid glycoside and uses thereof.

BACKGROUND ART

There has always been a considerable interest in volatile aromatic components of coffee. It has been reported that a part of the volatile aromatic components exists in the coffee fruit or green coffee beans as glycoside binding to sugar. Since the glycoside is an aroma precursor, the volatile aromatic component is released to provide aroma in response to maturity or physical damage. There have been reports of glycosides in the coffee fruit or green coffee beans being aroma precursors, but the majority of the reports are on glycosides having monoterpene or diterpene compounds as aglycones. Non-Patent Document 1 discloses that 3(S)-linalool-3-O-β-D-glucopyranosyl-β-D-apiofuranoside and 3(S)-linalool-3-O-β-D-glucopyranosyl-β-D-arabinofuranoside exist in green coffee beans as monoterpene aroma precursor. In addition, Non-Patent Documents 2 and 3 disclose that 3'-O-β-D-glucopyranosyl-2'-O-isovaleryl-2-O-β-D-glucopyranosyl-atractylogenin, 2-O-β-D-glucopyranosyl-atractylogenin, and 2'-O-isovaleryl-β-D-glucopyranosyl-atractylogenin exist in coffee beans as diterpene aroma precursor or an isovaleric acid aroma precursor. It is also reported that a glycoside having methyl crotonic acid or isovaleric acid as an aglycone exists in coffee fruits or green coffee beans (Non-Patent Document 4). Non-Patent Document 4 discloses 3-methylbutanoyl-1-O-β-D-glucopyranosyl-β-D-apiofuranoside, 3-methylbutanoyl-6-O-α-D-glucopyranosyl-β-D-fructofuranoside, and 3-methylbut-2-enoyl-1-O-β-D-glucopyranosyl-β-D-apiofuranoside.

CITATION LIST

Non-Patent Documents

Non-Patent Document 1: B. Weckerle, G. Toth, P. Schreire, Eur Food Res Technol (2003) 216:6-10
Non-Patent Document 2: Hans Gerhard Maier, Helga Wewetzer, Z. Lebensm. Unters. Forsch, 167, 105-107 (1978)
Non-Patent Document 3: Bradbury A. G. W., Balzer H. H., Colloq. 18th Sci. Int. Cafe, (1999) 71-77
Non-Patent Document 4: Bernhard Weckerle, Tamas Gati, Gabor Toth, Peter Schreier, Phytochemistry 60 (2002) 409-414

SUMMARY OF INVENTION

Technical Problem

However, the existence of glycosides having methyl crotonic acid or isovaleric acid as aglycones in coffee fruits or green coffee beans is not known except for the disclosures in Non-Patent Documents 2, 3 and 4. The object of the present invention is to provide a novel organic acid glycoside existing in coffee and uses thereof.

Solution to Problem

To solve the above problem the present inventors initiated studies of coffee that received high marks for flavor in the sensory assessment. After extensive studies, surprisingly, they found that an unknown glycoside exists in the high-quality coffee beans. The present inventors completed the present invention based on this finding.

The present invention relates to the following without being limited thereby.

(1) A compound having a structure represented by formula 1:

[Formula 1]

wherein, each of $R^1$ to $R^7$ is independently selected from a group consisting of H, OH, $NH_2$, $OCH_3$, $OC(O)CH_3$, and $NHCOCH_3$;
A is selected from $C_1$ to $C_6$ alkyl or $C_1$ to $C_6$ alkenyl, and the $C_1$ to $C_6$ alkyl or $C_1$ to $C_6$ alkenyl may be substituted by methyl or ethyl.
(2) The compound according to (1), wherein $R^1$ to $R^7$ is OH; and
A is selected from a group consisting of methyl, ethyl, propyl, butyl, pentyl, ethenyl, propenyl, butenyl, and pentenyl, and the ethyl, propyl, butyl, pentyl, propenyl, butenyl, and pentenyl may be substituted by methyl or ethyl.
(3) The compound according to (1) or (2), wherein A is propyl or propenyl, and the propyl or propenyl may be substituted by methyl.
(4) The compound according to any one of (1) to (3) selected from 3-methyl-2-butenoyl-β-gentiobioside or 3-methyl-butanoyl-β-gentiobioside.
(5) A composition comprising a compound according to any one of (1) to (4).
(6) The composition according to (5) for use in improving flavor of coffee beans or extracts obtained from coffee beans.
(7) The composition according to (5) or (6) that is mixed with coffee beans or extracts obtained from coffee beans.
(8) A method for improving flavor of extracts obtained from coffee beans comprising:
  mixing coffee beans or extracts obtained from coffee beans with a compound according to any one of (1) to (4) or a composition according to any one of (5) to (7).
(9) A method for evaluating quality of coffee beans or extracts obtained from coffee beans comprising:
  detecting a compound according to any one of (1) to (4) in coffee beans or extracts obtained from coffee beans.
(10) A method for identifying or estimating a variety of coffee comprising:
  detecting a compound according to any one of (1) to (4) in coffee beans or extracts obtained from coffee beans.

Advantageous Effects of Invention

It was confirmed that the organic acid glycosides found by the present inventors are novel, and they can be used to improve flavor of extracts obtained from coffee beans. It was also confirmed that content of the glycosides is correlated with the quality of the green coffee beans, and thus the glycosides can be used to estimate or evaluate quality of coffee beans or extracts obtained from coffee beans. Further, it was also confirmed that the content of the glycosides is correlated with the variety of the green coffee beans, and thus variety of coffee can be identified or estimated from coffee beans or extracts obtained from coffee beans. These matters were not predictable from the prior art.

DESCRIPTION OF EMBODIMENTS

Novel Glycoside

The present invention relates to a compound. The compound is a novel glycoside having a structure represented by the following formula:

[Formula 2]

Wherein, each of $R^1$ to $R^7$ is independently selected from a group consisting of H, OH, $NH_2$, $OCH_3$, $OC(O)CH_3$, and $NHCOCH_3$. For example, each of $R^1$ to $R^7$ is preferably, independently selected from H, OH, $NH_2$, $OCH_3$ and $OC(O)CH_3$, and more preferably, independently selected from OH. A is selected from $C_1$ to $C_6$ alkyl or $C_1$ to $C_6$ alkenyl, wherein the $C_1$ to $C_6$ alkyl or $C_1$ to $C_6$ alkenyl may be substituted by methyl or ethyl. The $C_1$ to $C_6$ alkyl is, for example, methyl, ethyl, propyl, butyl, pentyl, or hexyl, preferably ethyl, propyl, or butyl, more preferably propyl, or butyl, and even more preferably propyl, which may be substituted by methyl or ethyl; each of $C_1$ to $C_6$ alkenyl is, for example, ethenyl, propenyl, butenyl, pentenyl or hexenyl, preferably ethenyl, propenyl, or butenyl, more preferably propenyl, or butenyl, and even more preferably propenyl, which may be substituted by methyl or ethyl. In this specification, the compound of the present invention and the glycoside of the present invention have the same meaning, and they are treated as interchangeable terms.

An embodiment of the compound of the present invention is, for example, one in which each of $R^1$ to $R^7$ is OH, and A is propyl or propenyl which may be substituted by methyl. Specific examples of the compound of the present invention include 3-methyl-2-butenoyl-β-gentiobioside (also referred to as methyl crotonyl gentiobioside) or 3-methyl-butanoyl-β-gentiobioside (also referred to as isovaleryl gentiobioside).

The glycoside consists of aglycone and glycone. As an example, the methyl crotonyl gentiobioside is comprised of methyl crotonic acid as an aglycone and gentiobiose as a glycon, wherein the the methyl crotonic acid and the gentiobiose bound via ester bond. As another example, the isovaleryl gentiobioside is comprised of isovaleric acid as an aglycone and gentiobiose as a glycon, wherein the isovaleric acid and the gentiobiose bound via ester bond. These two glycosides are non-volatile, but when the aglycone and the glycone are cut off, the volatile methyl crotonic acid and isovaleric acid are respectively released. The methyl crotonic acid and the isovaleric acid are components of plant essential oil. Thus, the compound of the present invention may be used as a precursor of aroma.

The compound of the present invention may be manufactured by a chemical synthesis using a method known to a person skilled in the art, or it may be manufactured by extraction from a natural source. When manufacturing the compound of the present invention from a natural resource, plants can be used as a starting material. Plants that may be used include *Coffeas*, such as *Coffea arabica, Coffea canephora* var. *robusta, Coffea liberica*. When manufacturing the compound of the present invention from *Coffea*, it is possible to use a fruit from the *Coffea* or a green coffee bean from the fruit. A green coffee bean used in the present specification is a bean obtained by drying a coffee fruit under the sun followed by being threshed, or a bean obtained by removing a pulp from a fruit, followed by washing with water, drying, and threshed. It is also possible to manufacture the compound of the present invention from the fruit skin or pulp that has been removed from coffee fruits in the manufacture of green coffee beans. The fruit skin and the pulp are usually thrown away in the manufacture of green coffee beans. Thus, if the fruit skin or the pulp is used as starting material in the manufacture of the compound of the present invention, it leads to an effective use of waste.

In terms of improving production efficiency, it is preferable to use coffee fruits or green coffee beans with a high content of the objective compound. Such coffee fruits or green coffee beans include coffee fruits or green coffee beans, aroma of which is highly appreciated. Such coffee fruits or green coffee beans include, for example, mocha, blue mountain, geisha. It is also possible to perform a preliminary measurement of the content of the objective compound in coffee fruits or green coffee beans, and select coffee fruits or green coffee beans with a high content of the objective compound.

A solvent may be used to extract the compound of the present invention from coffee fruits, green coffee beans or fruit skin or pulp. Any solvent may be used as long as the compound of the present invention is extracted. Examples include an aqueous solution or an organic solvent, more specifically, a buffer or alcohols, which can be used alone or in a combination of two or more. Commercially available alcohols are convenient, and lower alcohol (methanol, ethanol, propanol, isopropanol, butanol, isobutanol, etc.), liquid polyvalent alcohol (1,3-butylene alcohol, propylene glycol, glycerol, etc.) may be used. Water-containing lower alcohol and lower alcohol are preferable in the present invention. The amount of solvent to be used may be varied according to amount of the starting material to be treated and the content of the objective compound in the starting compound. For example, 1 to 1000 mL, preferably 1 to 100 mL of solvent may be used for 1 g of the starting material.

The purity of the compound of the present invention extracted from the starting material may be increased, if necessary. The purity may be increased by purification of the extract. The purification of the extract may be performed by any method known to a person skilled in the art, for example, chromatography. Examples of chromatography include ion exchange chromatography, hydrophobic chromatography, hydrophilic chromatography, gel filtration chromatography. Purity may be assessed by a high performance liquid chromatography, or LC-MS which is a combination of the high performance liquid chromatography and a mass spectrometry.

The chemical structure of the compound of the present invention may be analyzed using methods well known to a person skilled in the art, such as NMR and mass spectrum analysis.

<Composition Comprising Novel Glycoside>

The present invention provides a composition comprising the compound of the present invention. Because the compound of the present invention is a glycoside, it may be used as a precursor of aroma. In other words, the aroma component can be released by cutting off the bond between the aroma component and the sugar moiety in the compound of the present invention. Any method may be used for cutting off the bond between the aroma component and the sugar moiety in the compound of the present invention. Such method includes means that utilize acids, alkali, heat or enzymes. A hydrolytic enzyme may be used as an enzyme for cutting off the bond between the aroma component and the sugar moiety. Enzymes generally have high substrate specificity, so it is preferable to select a suitable enzyme according to a glycoside to efficiently cut off the bond. Enzymes that may be used for cutting off the bond between the aroma component and the sugar moiety in the compound of the present invention include enzymes with glucosidase activity or glycoside hydrolysis activity.

The composition of the present invention may include other components. Such other components include those approved as food additives, and those that are not approved as food additives but are recognized as safe by being eaten over the past. Examples include preservatives, excipients, sweeteners, pH adjustors, etc. Specific examples of preservatives include glycine, sodium acetate, sodium benzoate, and protamine. Specific examples of excipients include dextrin, and starch. Specific examples of sweeteners include oligosaccharide, glucose, fructose, stevia, aspartame, etc. Specific examples of pH adjustors include phosphoric acid, citric acid, hydrochloric acid, acetic acid, ammonia, carbonic acid, lactic acid, etc. In one embodiment, the composition of the present invention include dextrin, oligosaccharide or citric acid in addition to the compound of the present invention. The composition of the present invention may be in any form. For example, it may be in the form of powder, liquid, tablets, granule, capsules or gel, etc.

It is noted that the compound of the present invention exists in an amount of 0.00000001 to 0.00001 wt % in the coffee fruit/fruit skin, and 0.00001 to 0.1 wt % in green coffee beans. The composition of the present invention may comprise the compound of the present invention at the same amount as the coffee fruit or green coffee beans. The composition of the present invention may comprise the compound of the present invention at a different amount from the coffee fruit or green coffee beans.

<Improving Flavor>

The compound or composition of the present invention may be used to improve flavor. Flavor as referred to in this specification is a clean, off-flavor-free savor with a balanced acidity and sweetness. Improving flavor refers to providing a more preferable flavor. Examples include enhancing the entire flavor, supplementing an insufficient flavor by enhancing a specific aroma component, or adding a distinctive flavor. The compound or composition of the present invention is applicable to food in general to improve flavor, and it may be preferably applied to improve flavor of coffee, beer, wine, whisky, etc., and it may be preferably applicable to improve flavor of coffee. When referring simply to "coffee" in this specification, the term broadly encompasses products and processed products relating to coffee such as coffee fruit, green coffee beans, roasted coffee beans, extract obtained from coffee fruit, extract obtained from green coffee beans, and extract obtained from roasted coffee beans. Further, when referring to "coffee beans" in this specification, it encompasses coffee fruit, green coffee beans, roasted coffee beans and ground products thereof, beans of *Coffea* and processed products thereof.

When the compound or composition of the present invention is applied for improving the flavor of coffee, it may be used in any step of coffee production. For example, coffee beans or an extract obtained from coffee beans may be mixed with the compound or composition of the present invention. The compound or composition of the present invention may be applied before harvesting coffee fruit to the root, trunk, leaves or the fruit, thereby increasing the content of the compound of the present invention in the coffee fruit.

In one embodiment, after green coffee beans and the compound or composition of the present invention are mixed together, the green coffee beans may be roasted to cut off the bond between aroma component and the sugar moiety in the compound of the present invention by the heat of roasting, and thereby releasing the aroma component. Thus, aroma of the roasted coffee beans may be improved. In another embodiment, the roasted coffee beans or the ground product thereof is mixed with the compound or composition of the present invention, then, hot water is poured to cut off the bond between aroma component and sugar moiety in the compound of the present invention by the heat of the hot water, and thereby releasing the aroma component to improve the flavor of the extract (also known as drip coffee) obtained from the roasted coffee beans or the ground product thereof. As another example, the extract obtained from coffee beans and the compound or composition of the present invention may be mixed, and then the mixture is heated at an appropriate timing before drinking to cut the bond between aroma component and sugar moiety in the compound of the present invention, so that the aroma may be released at a desired timing. When using the compound or composition of the present invention to improve flavor, the compound or the composition of the present invention may be mixed with a target of application so that the concentration of the free flavor component is, for example, 0.01 to 100 ppb, preferably 0.1 to 30 ppb, more preferably 0.1 to 10 ppb. Note that a free organic acid may be given as an example of a free aroma component, and methyl crotonic acid and isovaleric acid may be given as examples of the free organic acid.

<Coffee Quality Assessment>

The compound of the present invention may be used for quality assessment of coffee. The inventors of the present invention were the first to find that the compound of the present invention exists in coffee beans, and further found that the amount of the compound of the present invention is correlated with the quality of coffee. That is, it is discovered that coffee with a high content of the compound of the present invention is high quality. The compound of the present invention may be a precursor of aroma, so coffee with a high content of the compound of the present invention will release a large quantity of aroma component by heat treatment in roasting or extraction, and thus, is considered to contribute to quality, without being limited thereby. The quality assessment by the compound of the present invention includes extracting the compound of the present invention from coffee, detecting the compound, quantifying the compound, and then comparing the quantified value with that of a control. Quality assessment may be performed by using coffee beans or an extract obtained from coffee beans, and it is preferable to use green coffee beans, roasted coffee beans, ground product of roasted coffee beans, an extract obtained from green coffee beans or an extract obtained from roasted coffee beans, more preferably, green coffee beans or roasted coffee beans, and further preferably, green coffee beans. In one embodiment, quality assessment may be performed by detecting the compound of the present invention in green coffee beans, by quantifying the amount of the compound, and by comparing with control green coffee beans with medium-quality. In another embodiment, the compound of the present invention is detected and quantified using a part of green coffee beans subjected to assessment, while roasted beans are prepared from the remainder of the green coffee beans and graded by the cupping score to consider the relation between the compound of the present invention and the flavor of coffee. The "cupping score" means rating of flavor in line with the protocol of SCAA (Specialty Coffee Associate of America).

Further, the compound of the present invention exists in the fruit skin or pulp of coffee fruit. Similar to green coffee beans, the content of the compound of the present invention in the fruit skin or pulp is considered to vary depending on quality of coffee quality. Hence, the coffee quality may be assessed by using fruit skin, pulp or coffee fruit, as well as by using green coffee beans. It is possible to classify coffee fruit based on content of the compound of the present invention by assessing the fruit skin, pulp, coffee fruit or extracts thereof, and thereby obtaining green coffee beans, which are controlled in quality. In one embodiment, the coffee fruit may be classified by detecting and quantifying the compound of the present invention in the fruit skin and/or pulp, and by comparing the content of the compound of the present invention with that of a control fruit skin and/or pulp with medium-quality.

<Identification or Evaluation of Coffee Variety>

The compound of the present invention may be used to identify or evaluate the coffee variety. It is often difficult to distinguish the coffee variety from the appearance of coffee. The inventors of the present invention found that the content of the compound of the present invention in green coffee beans differ depending on variety of coffee. In other words, the content of the compound of the present invention may be used as an index to identify or evaluate the coffee variety. Identifying or evaluating variety of coffee comprises extraction, detection or quantification of the compound of the present invention from coffee, and then, referencing to a standard value set for each variety. For example, when the quantified amount in coffee sample is within or close to a range of a standard value of a specific variety, it is possible to identify or evaluate that variety of the coffee sample is that specific variety.

Furthermore, identification or evaluation of coffee variety may be performed by coffee beans or an extract obtained from coffee beans. For example, identification or evaluation of coffee variety may be performed by extracting the compound of the present invention from roasted coffee beans, an extract obtained from green coffee beans or an extract obtained from roasted coffee beans, detecting and quantifying the compound, and referring to a standard value set for each variety.

In addition, the compound of the present invention exists in the fruit skin or pulp of coffee fruit. The content of the present invention in the fruit skin or pulp may differ according to coffee quality, similar to the case in green coffee beans. Hence, the coffee variety may be identified or evaluated by using the fruit skin, pulp or coffee fruit, similar to the case in green coffee beans. Identification or evaluation of coffee variety may be performed by extracting the compound of the present invention from fruit skin, pulp or coffee fruit, by detecting and quantifying the compound, and by referring to a standard value set for each variety.

EXAMPLES

The present invention is described in detail based on Examples provided below. It is understood that the Examples do not have any intent to limit the present invention.

Example 1

Screening of Novel Compounds

<Purification of Compound>

Figure 1:
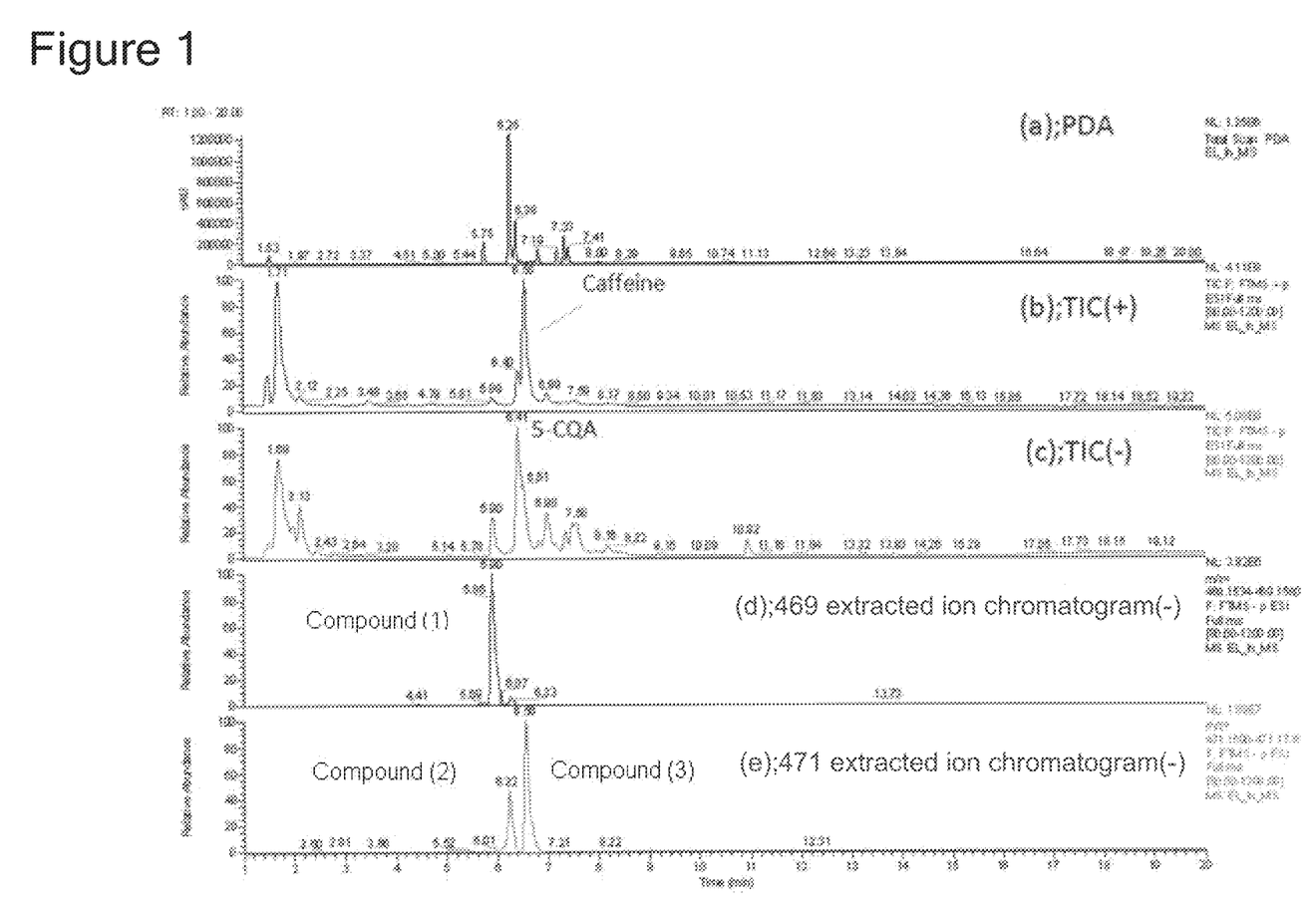
FIG. 1 shows the LC-MS chromatograph of extracts obtained from green coffee beans. (a) photodiode array (PDA); (b) total ion chromatogram (TIC) (positive mode); (c) total ion chromatogram (negative mode); (d) extracted ion chromatogram of m/z=489; (e) extracted ion chromatogram of m/z=471. 5-CQA: 5-caffeoylquinic acid (chlorogenic acid), FQA: feruloylquinic acid.

After freezing 1.6 kg of green coffee beans (Pacamala) with liquid nitrogen, the coffee beans were ground with a beads shocker, and the ground green coffee beans was treated with 5 L of hexane to remove lipophilic components. The ground beans treated with hexane were subjected to extraction using 8 L of 70% methanol (80° C., 2 h.), and the result was subjected to filtration using diatomaceous earth. The residue was subjected to extraction using 4 L of 70% methanol, and the result was filtered. The obtained filtrates were combined together and the mixture was concentrated to about ⅙ volume of the original volume. The concentration was conducted by a rotary evaporator. In addition, a part of the mixture was subjected to LC-MS to analyze composition in the mixtures (FIG. 1). High-resolution mass spectrometry was conducted by LC-MS using Q-Exactive (manufactured by Thermo Fisher Scientific Inc.) under the following conditions.

Column: KINETEX C18 (2.1 mm×250 mm, 1.7 μm, Phenomenex, CA)
Column temperature: 40° C.
Mobile phase A: water+0.1% formic acid
Mobile phase B: acetonitrile+0.1% formic acid
Concentration gradient of the mobile phase: Concentration of mobile phase B 5% (0-2 min), 5→55% (2-7.5 min), 55→100% (7.5 min-17 min), 100% (17 min-23 min), 100→5% (23 min-24 min), 5% (24 min-32 min)
Column flow rate: 0.2 mL/min
Ionization method: ESI, positive mode, negative mode
Spray voltage: 3.5 kV
Capillary temperature: 250° C.
Capillary voltage: 49V
Resolution: 70000 (MS, MSMS)
MS Scan range: m/z 80-1200
Collision energy: 15-45% normalize As a result, it was demonstrated existence of compounds having m/z 469 (FIG. 1(d)) and m/z 471 (FIG. 1(e)) as characteristic selected ions, namely compound (1) (m/z 469), compound (2) (m/z 471) and compound (3) (m/z 471).

The concentrated filtrate was loaded to 1 L of adsorption resin HP-20 (Mitsubishi Chemical Co.). The resin was washed with 3 L of water, then, elution was conducted by loading 3 L of 10% ethanol, and 3 L of 20% ethanol in a step-wise manner. The obtained fractions were subjected to LC-MS to identify fractions containing the compounds eluted. The result showed that compounds (1), (2) and (3) were eluted into the water wash fraction and the 10% ethanol fraction. The water wash fraction had a larger content of the compounds.

The water wash fraction having a larger content of compounds (1), (2) and (3) was loaded to 1.2 L of adsorption resin COSMOSIL 18-OPN (particle size 140 μm, manufactured by Nacalai tesque). The resin was washed with 500 mL of 0.1% formic acid solution, then, 3 L of 0.1% formic acid solution, 2.5 L of 10% ethanol containing 0.1% formic acid solution, and 2.5 L of 50% ethanol containing 0.1% formic acid solution were loaded to the resin in a step-wise manner to conduct elution. The three types of compounds were eluted into the fraction due to elution with 3 L of 0.1% formic acid solution and the fraction due to elution with 2.5 L of 10% ethanol containing 0.1% formic acid solution.

These fractions were loaded to 500 mL of an adsorption resin COSMOSIL 75C18PREP (particle size 75 μm, manufactured by Nacalai tesque). The resin was washed with 500 mL of 0.1% formic acid solution, then, 2 L of 0.1% formic acid solution, 2.5 L of 10% ethanol containing 0.1% formic acid solution, and 2.5 L of 20% ethanol containing 0.1% formic acid solution were loaded to the resin in a step-wise manner to conduct elution. The three types of compounds were eluted into the fraction due to elution with 2 L of 0.1% formic acid solution and the fraction due to elution with 2.5 L of 10% ethanol containing 0.1% formic acid solution.

These fractions were purified by the preparative HPLC shown below. Column used was Develosil-C30-UG-5 (Nomura Chemical Co., Ltd.) 20 mm×250 mm. Mobile phases used were A: water+0.1% formic acid, and B: 90% acetonitrile+0.1% formic acid. Flow rate was set to 15 ml/min, with B10% (0-14 min), a linear gradient of B10→B25% (14-34 min), and then B25% maintained for 10 min. A fraction containing compounds (1) and (2) that were eluted at 7-10 min and a fraction containing compound (3) that was eluted at 11-15 min were collected and respectively freeze-dried. The chromatography process was repeated 17 times.

The obtained freeze-dried products were respectively subjected again to chromatography using preparatory HPLC. The column used was Shodex Asahipak NH2P-20 20F (Showa Denko K.K.) 20 mm×300 mm, and the mobile phases used were A: water, and B: 90% acetonitrile. The flow rate was set to 10 ml/min. Purification of the fractions containing compounds (1) and (2) was performed under the condition: B100% (0-12 min), and a linear gradient of B100→B40% (12-90 min). Fractions containing compounds (1) and (2), that were eluted at 26-29 min, were collected and freeze-dried. The chromatography process was repeated twice. Purification of fractions containing compound (3) was performed under the condition: B 100% (0-12 min), and a linear gradient of B100→B40% (12-60 min). Fractions containing compound (3) that was eluted at 22-25 min were collected and freeze-dried. The chromatography process was repeated four times.

The obtained freeze-dried products were respectively subjected again to chromatography using preparatory HPLC. Develosil-C30-UG-5 (Nomura Chemical Co., Ltd.) 4.6 mm×150 mm was used with mobile phases A: water+0.1% formic acid, and B: 90% acetonitrile+0.1% formic acid. Flow rate was set to 1 ml/min. Isocratic elution was performed with B10% (0-30 min). Compound (1) eluted at 7-8 min, compound (2) eluted at 8-9 min, compound (3) eluted at 9-10 min were respectively collected to be freeze-dried. Consequently, compound (1) (2.3 mg), compound (2) (2.3 mg) and compound (3) (6 mg) were detected. When purity of the compounds (1) to (3) was determined by LC-MS, each compound was found to be highly purified.

<Determination of Chemical Structure>

1. Analysis by Spectrum Data of Instrumental Analysis

Purified compounds (1) to (3) were dissolved in DMSO-d6. $^1$H-NMR, $^{13}$C-NMR, $^1$H{$^{13}$C}-HSQC, $^1$H{$^{13}$C}-HMBC, TOCSY, DQF-COSY, $^1$H-NOESY and $^1$H-ROESY were measured using the NMR device (DMX-750 spectrometer) under the condition shown below.

TABLE 1

$^1$H NMR and $^{13}$C NMR chemical shift of Compounds 1, 2 and 3 measured in DMSO-$d_6$

| Position | 1 $^1$H NMR | 1 $^{13}$C NMR | 2 $^1$H NMR | 2 $^{13}$C NMR | 3 $^1$H NMR | 3 $^{13}$C NMR |
|---|---|---|---|---|---|---|
| Acyl moiety | | | | | | |
| 1 | — | 164.13 | — | 171.16 | — | 172.19 |
| 2 | 5.71 (s) | 114.91 | 2.24 (d; 7.0) | 42.29 | 2.20 (m) | 42.33 |
| 3 | — | 154.19 | 2.01 (m) | 24.83 | 1.99 (m) | 25.02 |
| 4 | 1.91 (s) | 26.9 | 0.92 (d; 6.7) | 22.02 | 0.91 (d; 6.7) | 22.03 |
| 5 | 2.13 (s) | 20.02 | 0.92 (d; 6.7) | 22.02 | 0.91 (d; 6.7) | 22.03 |
| Glucose moiety | | | | | | |
| 1' | 5.36 (d; 8.3) | 93.48 | 5.36 (d; 8.2) | 93.86 | 5.17 (d; 3.6) | 91.38 |
| 2' | 3.11 (m) | 72.22 | 3.11 (m) | 72.2 | 3.20 (m) | 71.4 |
| 3' | 3.23 (m) | 76.26 | 3.23 (m) | 76.33 | 3.48 (m) | 72.55 |
| 4' | 3.19 (m) | 69.16 | 3.18 (m) | 69.15 | 3.06 (m) | 70.03 |
| 5' | 3.39 (m) | 76.13 | 3.41 (m) | 76.15 | 3.90 (m) | 69.87 |
| 6'a | 3.98 (dd; 10.1, 1.0) | 67.85 | 3.96 (dd; 11.3, 1.0) | 67.77 | 4.24 (dd; 11.7, 1.3) | 63.36 |
| 6'b | 3.56 (dd; 10.1, 5.5) | — | 3.58 (dd; 11.3, 5.5) | — | 4.01 (dd; 6.0, 11.7) | |
| Glucose moiety | | | | | Fructose moiety | |
| 1" | 4.16 (d; 7.9) | 102.95 | 4.17 (d; 7.8) | 102.94 | — | 62.03 |
| 1ab' | — | — | — | — | 3.38 (m) | — |
| 2" | 2.96 (m) | 73.32 | 2.95 (m) | 73.34 | — | 103.79 |
| 3" | 3.11 (m) | 76.62 | 3.11 (m) | 76.6 | 3.87 (d; 8.1) | 76.79 |
| 4" | 3.04 (m) | 69.84 | 3.04 (m) | 69.85 | 3.73 (m) | 74.39 |
| 5" | 3.04 (m) | 76.74 | 3.04 (m) | 76.74 | 3.59 (m) | 82.65 |
| 6"a | 3.65 (dd; 11.2, 5.9) | 60.86 | 3.65 (dd; 11.2, 5.9) | 60.89 | 3.57 (m) | 62.50 |
| 6"b | 3.43 (m) | — | 3.44 (m) | — | 3.54 (m) | — |
| Sugar OH-group | | | | | | |
| 2'(OH) | 5.25 (d; 5.5) | — | 5.24 (d; 5.5) | — | 5.13 (d; 6.0) | — |
| 3'(OH) | 5.15 (d; 4.8) | — | 5.14 (d; 4.9) | — | 4.89 (d; 4.8) | — |
| 4'(OH) | 5.07 (d; 5.6) | — | 5.07 (d; 5.7) | — | 5.01 (d; 5.7) | — |
| 1"(OH) | — | — | — | — | 4.81 (t; 6.2) | — |
| 2"(OH) | 4.83 (d; 4.8) | — | 4.82 (d; 4.8) | — | — | — |
| 3"(OH) | 4.90 (d; 4.9) | — | 4.90 (d; 4.9) | — | 4.56 (d; 8.0) | — |
| 4"(OH) | 4.87 (d; 4.6) | — | 4.87 (d; 4.5) | — | 5.16 (d; 3.6) | — |
| 6"(OH) | 4.45 (t; 5.9, 5.9) | — | 4.44 (t; 5.9, 5.9) | — | 4.40 (t; 5.0, 5.0) | — |

In the $^1$H{$^{13}$C}-HMBC analysis, cross peaks were observed as follows for glycosides (1) to (3): for glycoside (1), glucose H-1' (δ5.36)→acyl group of the carbonyl carbon (δ164.13), and glucose H-1" (δ4.16)→glucose C-6' (δ67.85); for glycoside (2), glucose H-1' (δ5.36)→acyl group of the carbonyl carbon (δ171.16), and glucose H-1" (δ4.17)→glucose C-6' (δ67.85); and for glycoside (3), glucose H-6a' (δ4.01) and glucose H-6b' (δ4.24)→acyl group of carbonyl carbon (δ172.19), and glucose H-1' (δ5.17)→fructose C-2" (δ103.79).

Next, purified compounds (1) to (3) were subjected to LC-Orbitrap-MS set to conditions shown below, and their chemical structures were determined. Mass spectrometry (ESI-MS) (Table 2) and an analysis of main fragments of ESI mass spectra (ESI-MS/MS) (Table 3) were performed for compounds (1) to (3).

TABLE 2

Mass spectrometry of compounds (1) to (3)

| | 1 | 2 | 3 |
|---|---|---|---|
| m/z (observed) | 469.1554 | 471.1710 | 471.1709 |
| Composition | C18H29O14 | C18H31O14 | C18H31O14 |
| Theorical Mass | 469.1557 | 471.1714 | 471.1714 |
| Delta (ppm) | −0.64 | −0.85 | −1.06 |
| RDB equiv. | 4.5 | 4.5 | 4.5 |

TABLE 3

Main fragment of ESI mass spectra of compounds (1) to (3)

| m/z | 1 | 2 | 3 |
|---|---|---|---|
| 471.171 | | [M + HCO2H − H]$^-$ | [M + HCO2H − H]$^-$ |
| 469.155 | [M + HCO2H − H]$^-$ | | |
| 425.167 | | [M − H]$^-$ | [M − H]$^-$ |
| 423.151 | [M − H]$^-$ | | |
| 323.098 | [M − A$^a$ − H]$^-$ | [M − A$^a$ − H]$^-$ | [M − A$^a$ − H]$^-$ |
| 179.056 | [M − A − (Hexose − H2O) − H]$^-$ | [M − A − (Hexose − H2O) − H]$^-$ | [M − A − (Hexose − H2O) − H]$^-$ |

$^a$A = acyl moiety (for compound 1: 3-methylbut-2-enoic acid; compounds 2 and 3: 3-methylbutanoic acid)

2. Analysis of Sugar Composition

Figure 2:
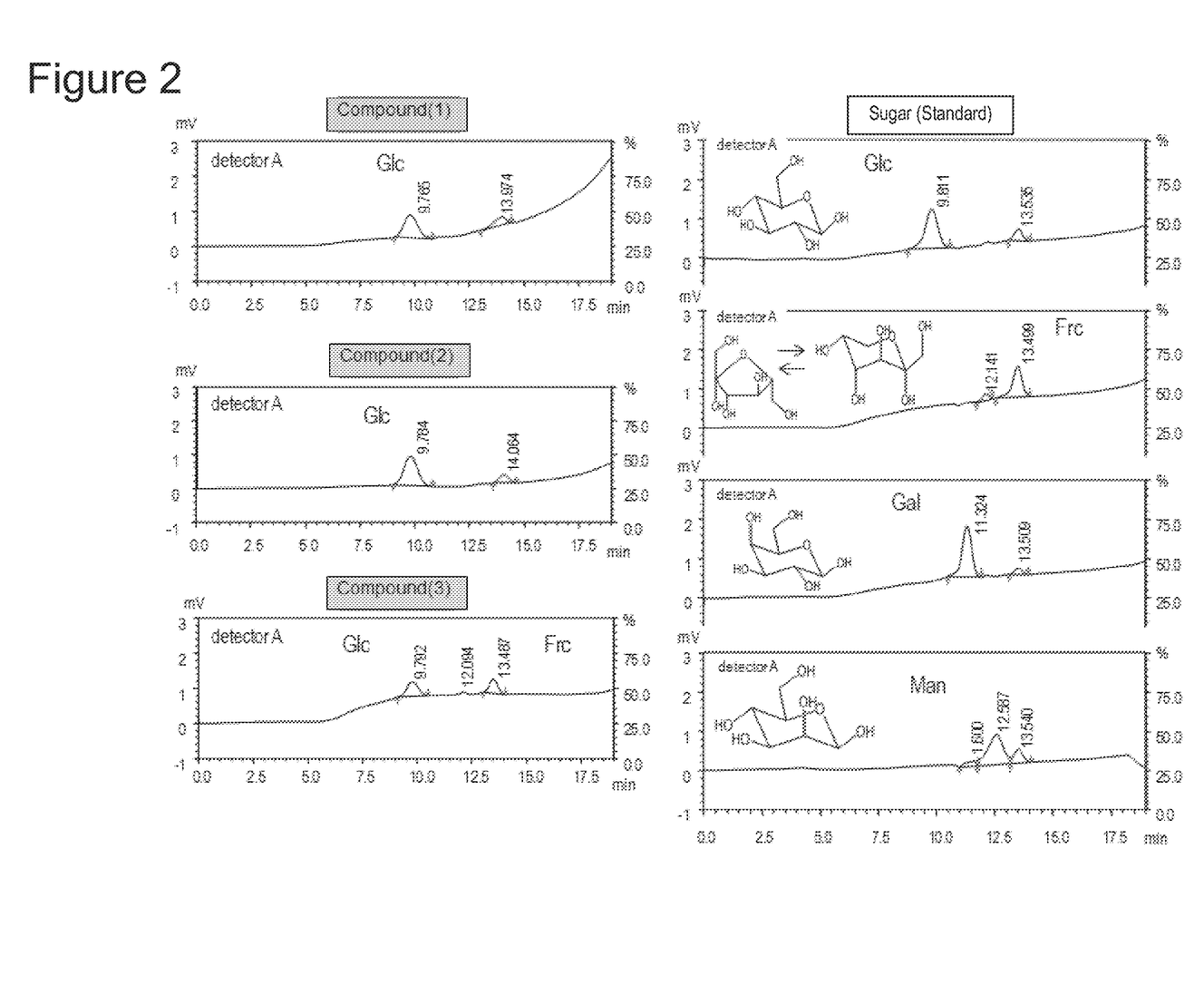
FIG. 2 shows the analysis of sugars produced by acid hydrolysis of glycosides (1) to (3) by LC-RI. Glc: D-glucose (retention time: about 9.8 min.); Frc: D-fructose (retention time: about 13.5 min.); Gal: D-galactose (retention time: about 11.3 min.); Man: D-mannose (retention time: about 12.6 min.).

Glycosides (1) to (3) were subjected to acid hydrolysis to analyze sugar composition. Glycosides (1) to (3) (at 200 μg each) were respectively dissolved in 0.2 mL of 6N—HCl, and incubated for an hour at 100° C. After the incubation, a part of the reaction solution was subjected to analysis using LC-RI under the following conditions. The standard sugars (D-glucose, D-fructose, D-galactose, D-mannose) were reacted under the similar conditions and were analyzed. The results are shown in FIG. 2. By comparing the LC retention time of the glycosides with that of the standard sugars, it was confirmed that glycoside (1) and glycoside (2) include glucose, and glycoside (3) includes glucose and fructose.

Condition of LC-RI Analysis:
Column: Shodex SUGAR SP080 Column (300×0.8 mm, particle size 7 μm)
Column temperature: 80° C.
Mobile phase: water (isocratic)
Column flow rate: 0.6 mL/min The analysis of the above data indicated that compounds (1) to (3) are respectively glycosides (1) to (3) with the following structures and compound names.
Glycoside (1): 3-methyl-2-butenoyl-β-gentiobioside
Glycoside (2): 3-methyl-butanoyl-β-gentiobioside
Glycoside (3): 3-methyl-butanoyl-sucroside

[Formula 3]

Glycoside(1)

Glycoside(2)

Glycoside(3)

As a result of searching compound database, glycosides (1) and (2) were found to be novel compounds that is unknown at this time. On the other hand, glycoside (3) was found to correspond to a compound reported in Non-Patent Document 4. Note that compounds (1) to (3) respectively mean the same as glycosides (1) to (3), and they may be used interchangeably in this specification.

Example 2

Improving Coffee Flavor

<Pyrolysis Reaction of Glycosides>
To serve as a model of thermal reaction caused by roasting green coffee beans, glycosides (1) to (3) purified by the method of Example 1 were respectively heated with a pyrolyzer (200° C., 10 min), and subjected to GC-MS. GC-MS was performed under the following condition.
Device: Double-shot Pyrolyzer (Pyolyzer) manufactured by Frontier Lab, 7890A (GC), 5975C (MS) manufactured by Agilent technologies
Pyrolysis Condition: 230° C., 10 min.
Column: DB-WAXetr (60 m×0.32 mm×0.25 μm) manufactured by GESTEL
Column Temperature: 40° C. (2 min)-40° C./min-250° C. (5 min)
Carrier gas: He
Transfer line: 250° C.
Ion source temperature: 230° C.
Scan Parameter: m/z=33 to 450
Split ratio: 10:1

Figure 3:
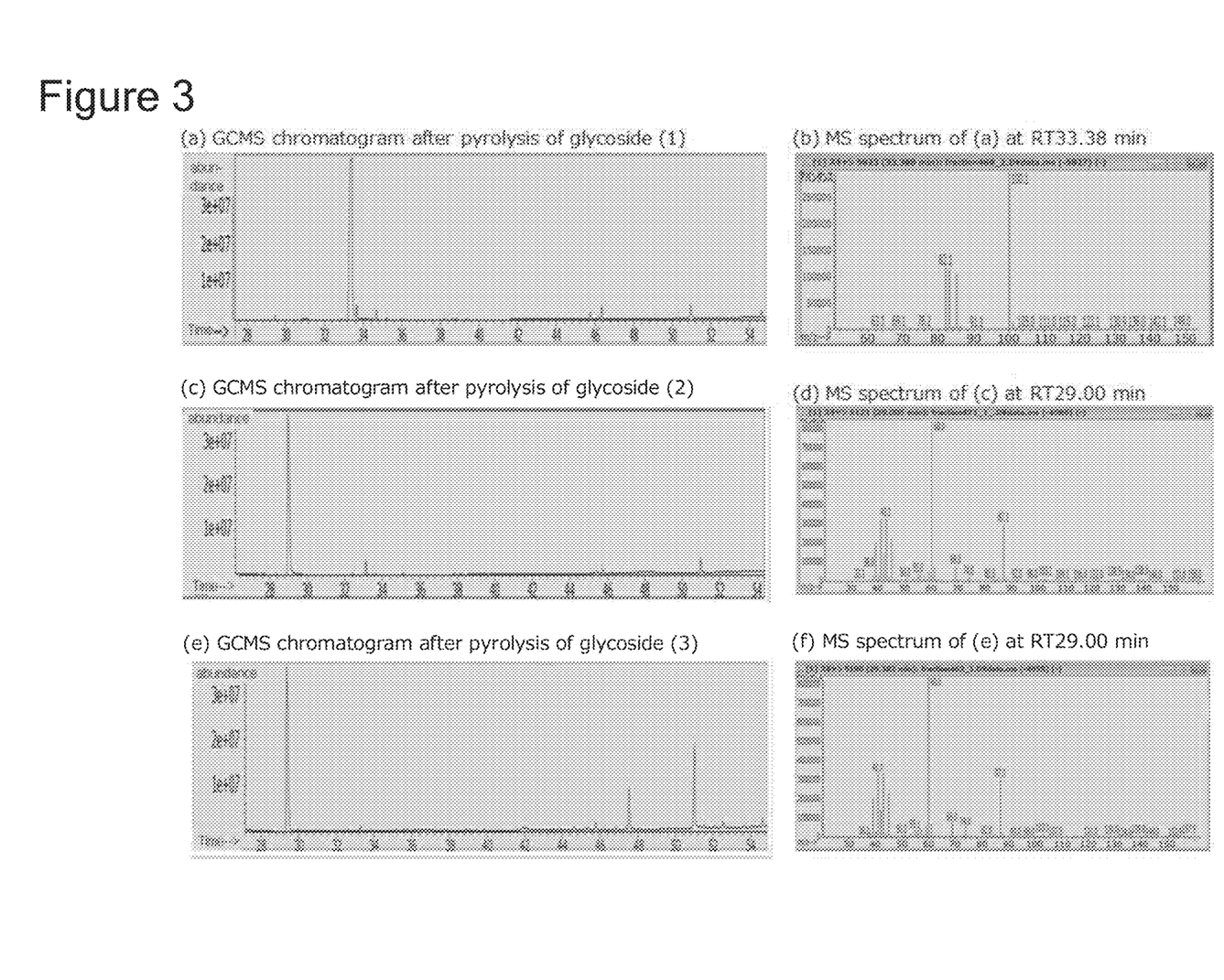
FIG. 3 shows volatile components detected by thermal treatment of glycosides (1) to (3). (a) The total ion chromatogram of the volatile component detected by thermal treatment of glycoside (1), and (b) the mass spectrum of the component detected at retention time 33.38 min. (c) The total ion chromatogram of the volatile component detected by thermal treatment of glycoside (2), and (d) the mass spectrum of the component detected at retention time 29.00 min. (e) The chromatogram of the volatile component detected by thermal treatment of glycoside (3), and (f) the mass spectrum of the component detected at retention time 29.00 min.

The result is shown in FIG. 3. When glycoside (1) was heated, a compound having a retention time (RT) of 33.38 min was detected. When glycoside (2) was heated, a compound having RT of 29.00 min was detected. When glycoside (3) was heated, a compound having RT of 29.00 min was detected. By performing a library search of mass spectrum, the compound of RT 33.38 min was confirmed to be methyl crotonic acid, and the compound of RT 29.00 min was confirmed to be isovaleric acid.

This result suggests that glycosides (1) to (3) are pyrolytically decomposed in roasting process of green coffee beans, generating methyl crotonic acid from glycoside (1), isovaleric acid from glycoside (2), and isovaleric acid from glycoside (3).

<Effect on Improving Coffee Flavor>
Effects of methyl crotonic acid generated by heating glycoside (1), and isovaleric acid generated by heating glycoside (2) on the flavor of coffee were examined.

After grinding 30 mL of roasted Guatemalan coffee beans with medium quality, 300 mL of hot water was dripped to the ground coffee beans. The resultant coffee extract was used as the control drip coffee. The drip coffee was mixed with methyl crotonic acid (10 ppb) and isovaleric acid (10 ppb) to conduct flavor assessment by six panels.

A sensory score was made for acidity, cleanness and bitterness in the aftertaste. In the flavor assessment, two standards were used: the control drip coffee (drip coffee obtained from the medium-quality, roasted Guatemalan coffee beans); and drip coffee obtained from coffee roasted beans made by roasting green coffee beans having a high flavor score, used in Example 3. The acidity, cleanness and the bitterness in the aftertaste of the control drip coffee were each assessed as 3 points. The acidity and cleanness of the drip coffee derived from green coffee beans with a high score in flavor were assessed as 5 points, and the bitterness in the aftertaste was assessed as 1 point.

Figure 4:
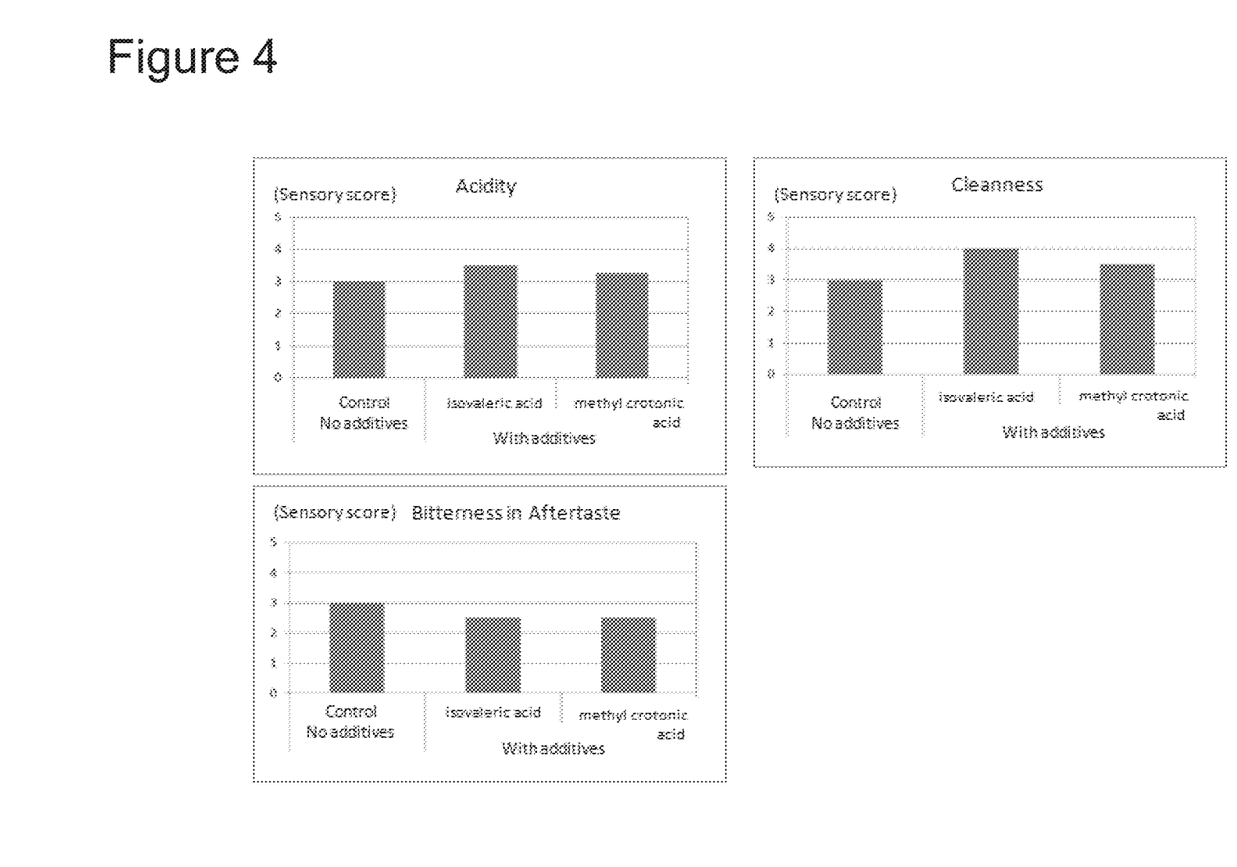
FIG. 4 shows the effect that methyl crotonic acid produced from glycoside (1) and isovaleric acid produced from glycoside (2) on the flavor of coffee. The sensory points in the diagram are the averages.

The result is shown in FIG. 4. In comparison to the control drip coffee, the drip coffee mixed with isovaleric acid and methyl crotonic acid scores high in acidity and cleanness, and low in bitterness in the aftertaste.

Further, the panelists commented that isovaleric acid particularly added a fruity acidity to the drip coffee, and that methyl crotonic acid added mildness to the drip coffee by reducing the bitterness in the aftertaste. These results clearly indicate that the flavor of coffee was improved by mixing methyl crotonic acid and isovaleric acid.

Example 3

Assessment of Coffee Quality

A study was made on whether glycosides (1) to (3) may be used to assess quality of coffee. The contents of glycosides in high-quality green coffee beans were compared with those of medium-quality green coffee beans to consider whether there is an interrelation between the quality of green coffee beans and the content of glycosides. The following green coffee beans were used in the study.

High-quality green coffee beans (green coffee beans with high flavor score): Jamaica blue mountain green coffee beans, defective beans were removed, screen 18

Medium-quality green coffee beans: Guatemalan green coffee beans, defective beans were removed, screen 18

An extract was obtained from green coffee beans according to the method described in Example 1, and analysis was performed by detecting a selected ion m/z 469, which is characteristic in glycoside (1), and a selected ion m/z 471, which is characteristic in glycosides (2) and (3), as indices.

Figure 5:
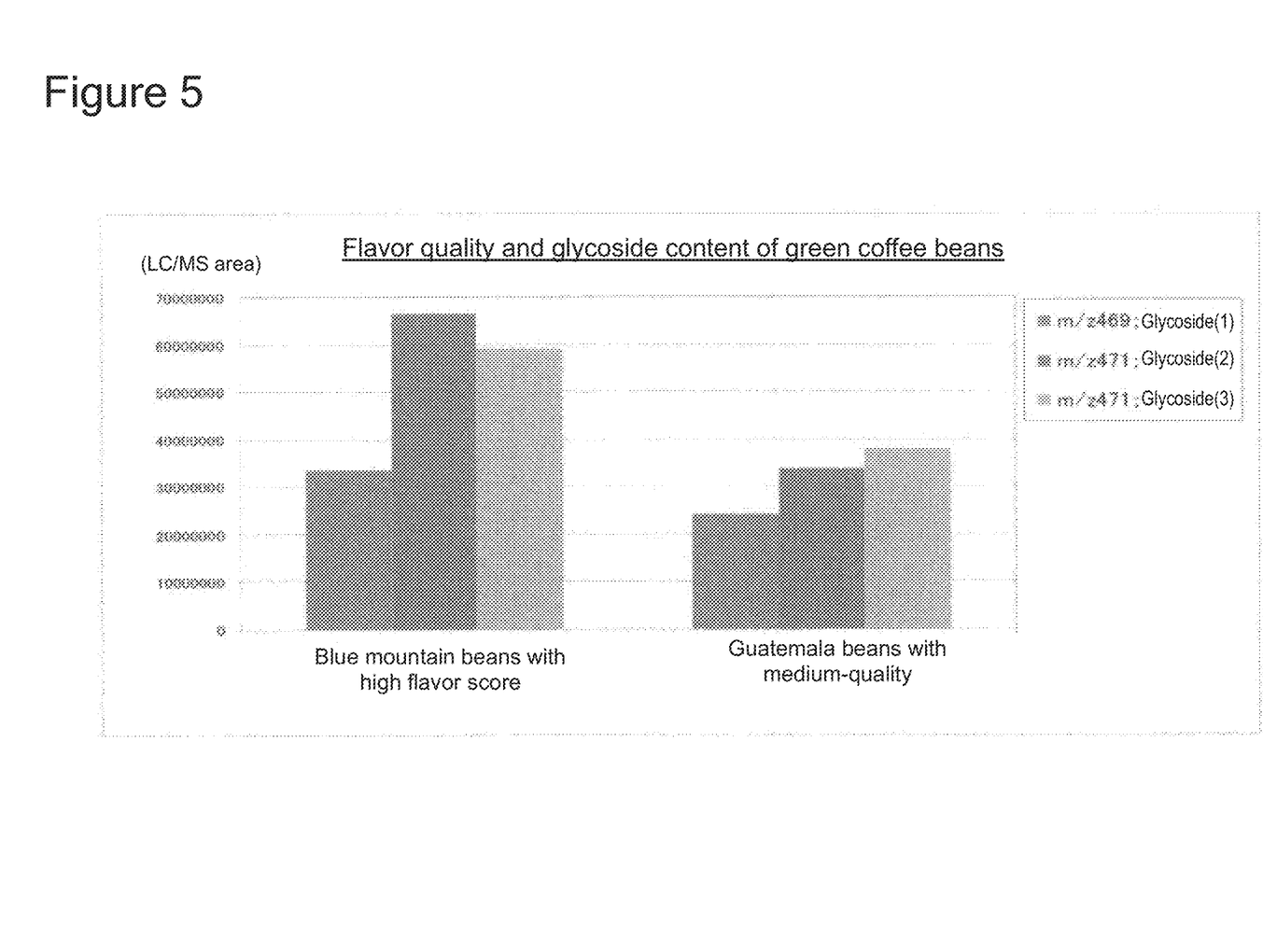
FIG. 5 shows the relationship between the content of glycoside in green coffee beans and the quality of the coffee. Glycoside (1) was detected by extracted ion chromatograph of m/z=469, and glycosides (2) and (3) were detected by extracted ion chromatograph of m/z=471.

The analysis result is shown in FIG. 5. The peak areas of m/z 469 and m/z 471 were high in high-quality green coffee beans relative to the medium-quality green coffee beans. In other words, it was shown that the contents of glycoside (1), glycoside (2) and glycoside (3) were high in high-quality green coffee beans compared to medium-quality green coffee beans.

It was thus shown that the content of one of glycoside (1), glycoside (2) or glycoside (3) may be used as an index to assess the quality of green coffee beans. It was also shown that the quality of green coffee beans may be assessed using the contents of glycosides (1) and (2), glycosides (2) and (3), glycosides (1) and (3) or glycosides (1) to (3) as indices.

Example 4

Quality Assessment of Coffee

Green coffee beans that differ in qualities were compared to research the correlation of the quality of green coffee beans and glycosides (1) to (3).

Thirty six types of Guatemalan green coffee beans were prepared and a part of each type of the Guatemalan green coffee beans was roasted (L value: 22-23), then a cupping score was assigned to each type of the green coffee beans according to the SCAA (Specialty Coffee Associate of America) protocol. In addition, the remains of each green coffee beans were frozen by liquid nitrogen, and ground by a beads shocker, then the ground product was treated with hexane. The ground product treated with hexane was treated with 70% methanol to obtain an extract. The extract was subjected to LC-MS set to the following conditions. The extract was measured at N=3.
Device: LC-MS-IT-TOF (Shimadzu)
Column: Luna-C18 (1.0 mm×250 mm, 5 µm, manufactured by Phenomenex, CA)
Column temperature: 40° C.
Mobile phase A: water+0.1% formic acid
Mobile phase B: acetonitrile+0.1% formic acid
Concentration gradient of the mobile phase: Concentration of mobile phase B 5% (0-2 min), 5→55% (2-7.5 min), 55→100% (7.5 min-17 min), 100% (17 min-23 min), 100→5% (23 min-24 min), 5% (24 min-32 min)
Column flow rate: 0.1 mL/min
Ionization method: ESI, positive mode, negative mode
Spray voltage: +4.5 kV (positive mode), −3.5 kV (negative mode)
Nebulizer gas flow rate: 1.5 L/min
CDL temperature: 250° C.
Heat block temperature: 250° C.
MS Scan range: m/z 80-800

Figure 6:
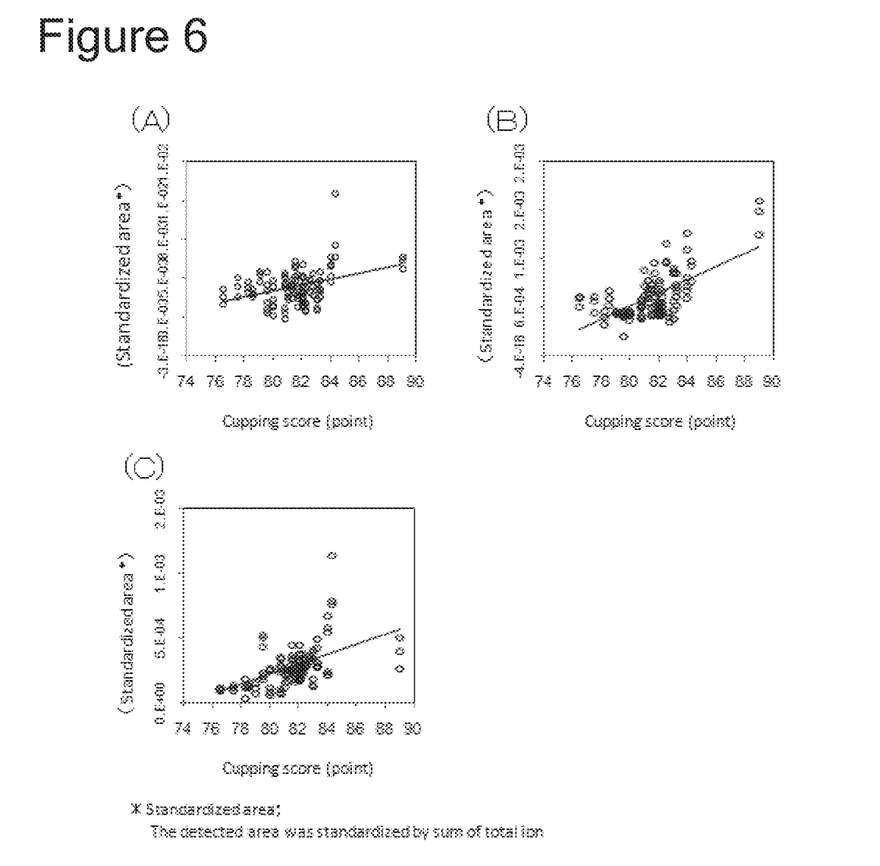
FIG. 6 shows the relationship between the cupping score and organic acid glycoside, with respect to green coffee beans. A: glycoside (1); B: glycoside (2); C: glycoside (3). The measurement was carried out at N=3.

Selected ion m/z 447 (positive mode), which is characteristic in glycoside (1), and selected ion m/z 449 (positive mode), which is characteristic in glycosides (2) and (3), were used as indices to identify peaks corresponding to glycosides (1) to (3) to measure the peak areas of each glycosides. The peak area for each glycosides was standardized by the sum of the total ion counts. Diagrams relating to the cupping score and the standardized peak area were created for each of glycosides (1) to (3) (FIG. 6). FIG. 6 showed that high quality beans tend to contain glycosides (1) to (3) at high amounts. As a typical example, the quantified values of glycosides (1) to (3) from green coffee beans with a cupping score of 81 points were as follows. Glycoside (1): 0.017 wt %, glycoside (2): 0.018 wt %, glycoside (3): 0.019 wt %.

The above result showed that there is a correlation between the peak areas of glycosides (1) to (3) and the cupping score. In other words, the existing amounts of glycosides (1) to (3) were used as indices for predicting coffee quality.

Example 5

Identification or Evaluation of Coffee Variety

It was studied whether there is a difference in the contents of glycosides among different varieties of coffee. The following green coffee beans were used. Glycosides (1) to (3) were extracted, detected and quantified according to the method of Example 1.

TABLE 4

| No | Green Coffee Beans |
|---|---|
| 1 | Guatemala Pacamala |
| 2 | Guatemala SHB |
| 3 | Jamaica Typica |
| 4 | Brazil 4/5 |
| 5 | Vietnam G1 |

Figure 7:
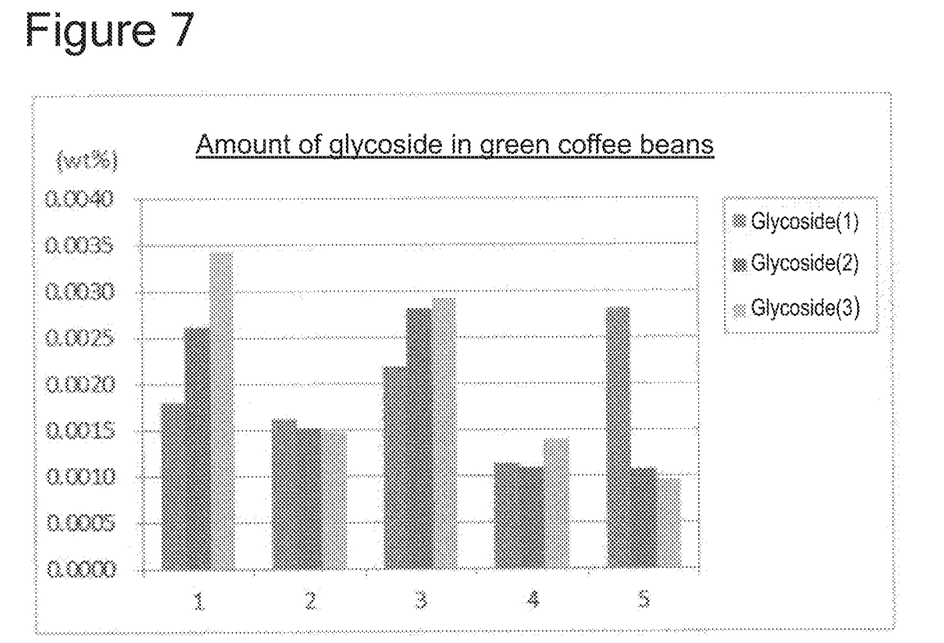
FIG. 7 shows the relationship between the glycoside content in green coffee beans and coffee varieties. 1: Guatemala Pacamala; 2: Guatemala SHB; 3: Jamaica Typica; 4: Brazil 4/5; 5: Vietnam G1.

The result is shown in FIG. 7. It was found that the contents of glycosides (1) to (3) differ greatly between the different varieties. In other words, it was shown that the content of glycoside (1), glycoside (2) or glycoside (3) may be used as an index to identify or evaluate the variety of green coffee beans. Furthermore, it was shown that it is possible to identify or evaluate the variety of green coffee beans by combining the contents of glycosides (1) and (2), glycosides (2) and (3), glycosides (1) and (3) or glycosides (1) to (3).

In addition, the ratio of the contents of glycosides (1) to (3) was found to have characteristics in each variety. It was thus shown that the variety of green coffee beans may be identified or evaluated by using the ratio of the contents of glycosides (1) to (3) as indices.

Example 6

Organic Acid Glycoside in Pulp or Fruit Skin of Coffee

This example was intended to extract organic acid glycosides from the pulp or fruit skin of coffee, and to confirm their existence.

Figure 8:
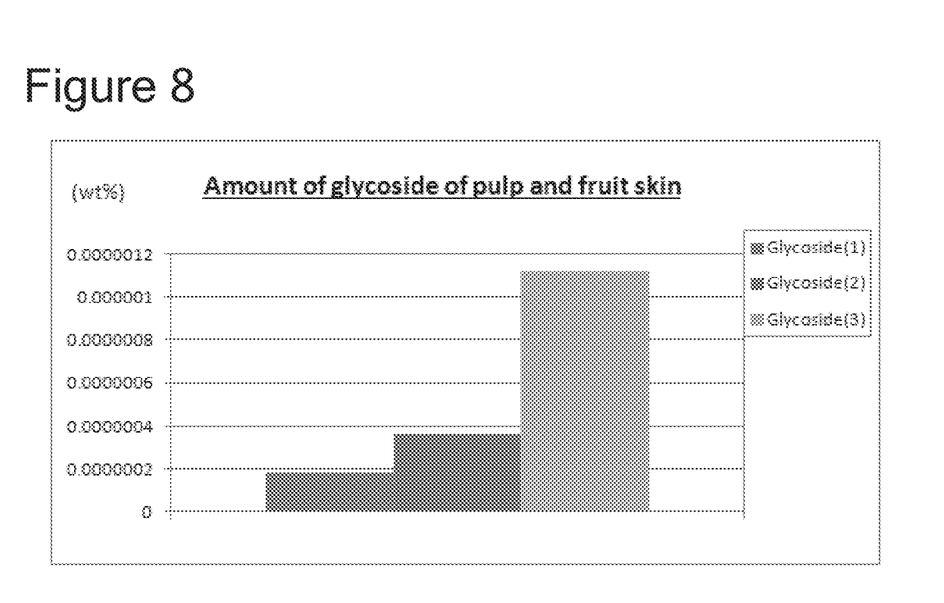
FIG. 8 shows the amount of glycosides in the pulp and fruit skin of the coffee fruit. Glycoside (1) was detected by extracted ion chromatograph of m/z=469, and glycosides (2) and (3) were detected by extracted ion chromatograph of m/z=471.

The coffee fruit (variety: Red Catuai) was frozen with liquid nitrogen, separated into fruit skin/pulp and beans. The fruit skin/pulp was ground by a beads shocker to obtain an extract according to the method described in Example 1. Analysis was performed by setting selected ion m/z 469, which is characteristic in glycoside (1), and selected ion m/z 471, which is characteristic in glycosides (2) and (3), as indices (FIG. 8).

The result clearly indicated that glycosides (1) to (3) exist in the fruit skin/pulp as well. This means that the fruit skin/pulp may be used to extract glycosides, perform quality analysis of coffee, and identify or evaluate the variety of coffee.

The invention claimed is:

1. A method for improving the flavor of an extract obtained from a coffee bean comprising:
   mixing the coffee bean with a purified compound, the purified compound selected from the group consisting of 3-methyl-2-butenoyl-β-gentiobioside and 3-methyl-butanoyl-β-gentiobioside, thereafter, obtaining the extract from the coffee bean mixed with the purified compound; or
   obtaining the extract from the coffee bean, and mixing the extract with a purified compound, the purified compound selected from the group consisting of 3-methyl-2-butenoyl-β-gentiobioside and 3-methyl-butanoyl-β-gentiobioside.

2. A method for improving the flavor of a coffee bean extract comprising:
   mixing a coffee bean with (i) a purified compound, wherein the purified compound is selected from the group consisting of: 3-methyl-2-butenoyl-β-gentiobioside and 3-methyl-butanoyl-β-gentiobioside; and (ii) at least one food additive, wherein the food additive is selected from the group consisting of a preservative, an excipient, a sweetener, and a pH adjustor, thereafter, obtaining the extract from the coffee bean mixed with the purified compound and the at least one food additive; or
   obtaining the extract from the coffee bean, and mixing the extract with (i) a purified compound, wherein the purified compound is selected from the group consisting of: 3-methyl-2-butenoyl-β-gentiobioside and 3-methyl-butanoyl-β-gentiobioside; and (ii) at least one food additive, wherein the food additive is selected from the group consisting of: a preservative, an excipient, a sweetener, and a pH adjustor.

3. A method for improving the flavor of a coffee bean extract comprising:
   mixing a coffee bean with (i) a purified compound, wherein the purified compound is selected from the group consisting of: 3-methyl-2-butenoyl-β-gentiobioside, 3-methyl-butanoyl-β-gentiobioside, and 3-methyl-butanoyl-sucroside; and (ii) at least one food additive, wherein the food additive is selected from the group consisting of: a preservative, an excipient, a sweetener, and a pH adjustor, thereafter, obtaining the extract from the coffee bean mixed with the purified compound, and the at least one food additive; or
   obtaining the extract from the coffee bean, and mixing the extract with (i) a purified compound, wherein the purified compound is selected from the group consisting of: 3-methyl-2-butenoyl-β-gentiobioside, 3-methyl-butanoyl-β-gentiobioside, and 3-methyl-butanoyl-sucroside; and (ii) at least one food additive, wherein the food additive is selected from the group consisting of: a preservative, an excipient, a sweetener, and a pH adjustor.

4. The method according to claim 1, further comprising cleaving the bond between an aroma component and a sugar moiety in the purified compound by treating the purified compound with an acid, an alkali, heat, or an enzyme, thereby releasing the aroma component.

5. The method according to claim 2, further comprising cleaving the bond between an aroma component and a sugar moiety in the compound by treating the purified compound with an acid, an alkali, heat, or an enzyme, thereby releasing the aroma component.

* * * * *